(12) United States Patent
Brazier et al.

(10) Patent No.: US 10,388,476 B2
(45) Date of Patent: *Aug. 20, 2019

(54) PRESSURE RESPONSE MEMBRANE

(71) Applicant: BS&B SAFETY SYSTEMS LIMITED, Limerick (IE)

(72) Inventors: Geof Brazier, Woodbury, MN (US); Arnold Mundt, Tulsa, OK (US)

(73) Assignee: BS&B Innovations Limited, Limerick (IE)

(*) Notice: Subject to any disclaimer, the term of this patent is extended or adjusted under 35 U.S.C. 154(b) by 984 days.

This patent is subject to a terminal disclaimer.

(21) Appl. No.: 13/987,768

(22) Filed: Aug. 30, 2013

(65) Prior Publication Data
US 2015/0064515 A1    Mar. 5, 2015

Related U.S. Application Data

(62) Division of application No. 12/149,691, filed on May 6, 2008, now Pat. No. 8,525,055.

(60) Provisional application No. 60/924,306, filed on May 8, 2007.

(51) Int. Cl.
*H01M 2/34* (2006.01)
*H01H 35/34* (2006.01)
*H01M 2/12* (2006.01)
*G01N 19/00* (2006.01)

(52) U.S. Cl.
CPC .............. *H01H 35/34* (2013.01); *G01N 19/00* (2013.01); *H01M 2/1229* (2013.01); *H01M 2/345* (2013.01); *H01M 2200/20* (2013.01)

(58) Field of Classification Search
CPC ............................ G01N 19/00; H01M 2200/20

USPC .......................................................... 429/61

See application file for complete search history.

(56) References Cited

U.S. PATENT DOCUMENTS

| 2,798,130 | A | * | 7/1957 | Cox | H01H 35/343 |
| | | | | | 200/83 B |
| 5,570,803 | A | * | 11/1996 | Farwell | B65D 51/1638 |
| | | | | | 220/89.2 |
| 6,204,635 | B1 | * | 3/2001 | Sullivan | H01M 2/0426 |
| | | | | | 320/134 |
| 2010/0143770 | A1 | * | 6/2010 | Onnerud | H01M 2/1235 |
| | | | | | 429/50 |

OTHER PUBLICATIONS

Office Action, Chinese Application No. 2008800151004 (dated Jan. 5, 2017) (4 pages).

* cited by examiner

*Primary Examiner* — Stewart A Fraser
*Assistant Examiner* — Victoria H Lynch
(74) *Attorney, Agent, or Firm* — Finnegan, Henderson, Farabow, Garrett & Dunner, LLP

(57) ABSTRACT

Pressure response devices, systems, and associated methods. The pressure response device includes a flange portion, a central portion, and an angled frustum portion provided between the flange portion and the central portion, with the angled frustum portion configured to activate upon experiencing a predetermined pressure differential. Pressure response systems may include a projection, a conductive arch, or a photo emitter configured to indicate a response to the predetermined pressure differential. Pressure response device may be a battery device, with the pressure response member configured to form part of an electrical conducting path until a predetermined pressure condition is reached.

10 Claims, 14 Drawing Sheets

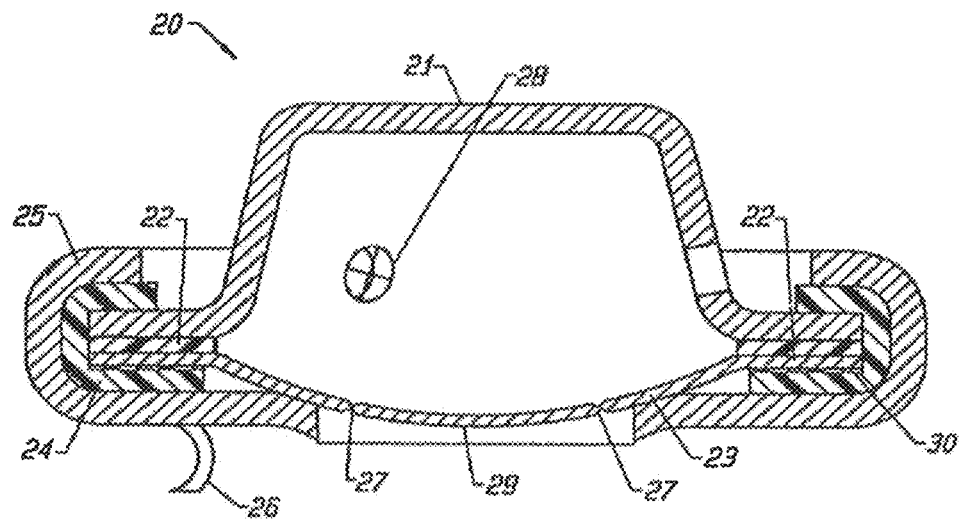
FIG. 1 — PRIOR ART
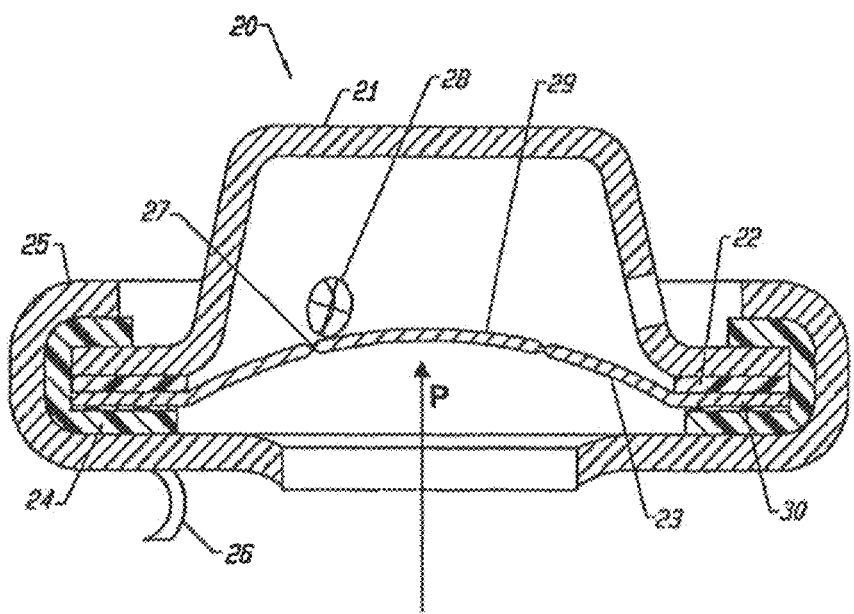
FIG. 2 — PRIOR ART

PRESSURE RESPONSE MEMBRANE

CROSS-REFERENCE TO RELATED APPLICATION

This is a division of U.S. application Ser. No. 12/149,691, filed Jul. 27, 2010, filed May 6, 2008, which claims the benefit of U.S. provisional application No. 60/924,306 filed May 8, 2007, all of which are incorporated herein by reference.

FIELD

The present disclosure relates generally to pressure response members. Specifically, the present disclosure relates to pressure response members that are buckled, collapsed, or otherwise displaced in response to experiencing a predetermined magnitude of fluid pressure.

BACKGROUND

There are many types of systems that process, transport, or utilize a pressurized fluid. To ensure the safety of these types of systems, each such system typically includes a safety device designed to prevent (or at least provide an alarm indication during) the over-pressurization of the system. In an emergency situation, where the fluid in the system reaches an unsafe level, the pressure of the fluid acts on the safety device to create an opening to release fluid from the system. Outside of creating an opening, the safety device may simply provide an alert warning, indicating that a dangerous over-pressure situation is occurring. In devices that actually rupture, or otherwise open to environment, venting fluid to the environment or a safety reservoir through the opening reduces the pressure in the system and prevents another portion of the system from failing due to the high pressure of the fluid.

Examples of commonly used safety devices include rupture disks and explosion panels. These safety devices can be attached to a pressurized system to expose a certain portion of the device to the pressurized fluid in the system. Often, a portion of the device exposed to the fluid is configured to rupture or tear when the fluid reaches a predetermined pressure. The tearing or rupture of the disk or panel creates an opening through which the pressurized fluid flows to reduce the pressure in the system. This type of safety device is, therefore, self-destructing and must be replaced after each use. Typically, to replace one of these safety devices, some disassembly of the system is needed so that the disk or panel can be properly engaged with the system.

In addition, where the safety device is designed to rupture or automatically open (i.e., a self-destructing safety device), production and formation often requires precise scoring or otherwise weakening the material of the device in order to ensure opening at a particular location and pressure. For example, rupture disk formation often includes scoring, cutting, etching, or thinning material of the device to outline a predetermined "burst pattern." This precise machining results in added manufacturing time and machinery, thereby increasing manufacturing costs.

In the field of "reverse buckling" rupture disk pressure relief devices, a concave/convex shaped structure has been used as a means of providing a reliable and reproducible pressure responsive device. Known "reverse buckling" devices are designed such that when the convex side of the structure is exposed to a predetermined overpressure force, the structure "buckles" and inverts causing the convex side to collapse into a concave shape. Moreover, at the predetermined overpressure force, the rupture disk is typically designed not only to invert, but also to open by means of a cutting device located downstream of the disk, or by virtue of a line of weakness produced by scoring, etching, or other means during the manufacturing process.

Within the broad category of concave/convex shaped structures used for reliable reverse buckling pressure response, there exist many shape subsets, such as, for example, a centered spherical dome, an offset spherical dome, a pyramid shape, and a truncated pyramid shape. The spherical dome shape, frequently used in known reverse buckling devices, suffers from a number of drawbacks. For example, a generally spherically shaped domed structure often only partially collapses during an over-pressure condition. In addition, a spherically shaped, partially domed structure may reverse in an irregular, or uneven, non-symmetrical manner, thereby leading to inconsistent results, particularly for smaller nominal sizes such as below 1"/25 mm diameter. Moreover, during shipping and packaging, the spherical shape is susceptible and often exposed to damage, or mishandling during shipping and packaging that adversely effects the desired response pressure (often leading to rupture or opening at a lower pressure than the set pressure). Finally, the scoring and etching required to form a reproducible burst pattern adds to the overall cost and profit associated with manufacturing.

There is a need for a pressure response structure that overcomes one or more of the deficiencies above and/or other deficiencies in the art.

SUMMARY

According to one embodiment, a pressure response device includes a flange portion, a central portion having an inlet side and an outlet side, and an angled frustum portion provided between the flange portion and the central portion. The angled frustum portion is configured to activate upon experiencing a predetermined pressure differential causing the movement of the central portion.

According to another embodiment, a pressure response system comprises a flange portion, a central portion, and an angled frustum portion provided between the flange portion and the central portion. The central portion is substantially flat, and a projection is operably attached to the central portion. The angled frustum portion is configured to activate without rupturing upon experiencing a predetermined pressure differential causing the movement of the central portion, and activation of the frustum portion causes the projection to indicate a pressure response.

According to another embodiment, a pressure response system includes a pressure response device having a flange portion, a central portion, and an angled frustum portion provided between the flange portion and the central portion. The angled frustum portion is configured to activate upon experiencing a predetermined pressure differential causing the movement of the central portion. A conductor is configured to make an electrical wire connection with the central portion before the angled frustum portion activates, and the electrical wire connection is interrupted when the angled frustum portion activates.

According to another embodiment, a battery device comprises an exterior contact terminal and a pressure response member positioned within the battery device, the pressure response member having a first configuration and a second configuration, the pressure response member including a central portion surrounded by an angled frustum portion.

The pressure response member forms part of an electrical conducting path within the battery device in the first configuration, and upon experiencing a predetermined pressure condition with the battery device, the pressure response member achieves the second configuration and no longer forms part of an electrical conducting path within the battery device.

According to another embodiment, a method of testing a pressure response system comprises providing a pressure response member including a flange portion, a central portion, and an angled frustum portion between the flange portion and the central portion, applying an increasing pressure differential to one surface of the central portion, and recording the pressure at which the angled frustum portion activates.

According to another embodiment, a method of responding to an overpressure situation comprises providing a pressure response member including a flange portion, a central portion, and an angled frustum portion between the flange portion and the central portion, wherein the pressure response member has a first configuration and a second configuration. The pressure response member is exposed in the first configuration to a pressure source, such that the pressure response member responds to a predetermined pressure in the pressure source by taking the second configuration.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments and together with the description, serve to explain the principles of the disclosure.

FIG. 1 is a cross-sectional view of a prior art reverse buckling device used in a system for interrupting a battery circuit.

FIG. 2 is a cross-sectional view of the prior art reverse buckling device of FIG. 1 after collapse of the reverse buckling device.

DESCRIPTION OF THE EMBODIMENTS

Figure 3A:
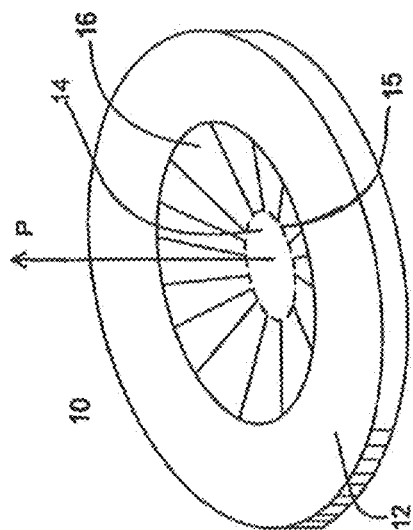
FIG. 3A is perspective view of a pressure response member, according to an embodiment of the disclosure.

Reference will now be made in detail to the present exemplary embodiments, examples of which are illustrated in the accompanying drawings. Wherever possible, the same reference numbers will be used throughout the drawings to refer to the same or like parts. The drawing figures of this application are intended to provide a general understanding of the working elements of the underlying system. Accordingly, unless explicitly stated, the figures do not represent a literal depiction of proportional dimensions or the precise locations for the illustrated inter-related components.

FIGS. 1 and 2 show cross-sectional views of a prior art reverse buckling device used in a system for interrupting a battery circuit. In particular, FIGS. 1 and 2 comprise two figures from U.S. Pat. No. 5,741,606 ("the '606 patent"), which is directed to an overcharge protection battery vent. The device operates to guard against the risk of explosion or the dangerous uncontrolled release of electrolytes in a battery cell device. Such devices are sometimes referred to as current interrupt devices, or "CIDs." In normal operation the reverse buckling device, in its original shape, constitutes part of the electrically conductive pathway of the battery circuit. In a short circuit situation, or any other dangerous, over-pressure situation that could lead to catastrophic battery failure due to increasing pressure, the reverse buckling disk of the '606 patent reverses to interrupt the conducting circuit and block the continued circuit path causing the dangerous over-pressure condition. Where the over-pressure condition becomes too great, the reverse buckling disk fails and ruptures along a predetermined burst pattern to vent the fluid to relieve the pressure.

FIG. 1 depicts a top portion of a battery terminal contact 21. According to FIG. 1, an electrically conducting path traverses conductive tab 26, conductive jacket 25, spherical, domed shaped reverse buckling disk 29, and resistor 22, and terminates at terminal contact 21. As seen in FIG. 2, when the pressure within a lower compartment (not shown) of the battery rises to a dangerous level (e.g., due to a dangerous battery malfunction), fluid pressure in the direction of arrow P eventually causes disk 29 to buckle and reverse. Upon its reversal, disk 29 no longer contacts conductive jacket 25. As a result, the conducting path is broken, thus removing the cause of the high pressure condition. If high pressure nonetheless remains or reaches a certain magnitude, disk 29 is further designed to rupture along scoring lines 27, resulting in the venting of fluid within the battery out of vent holes 28. Because disk 29 provides a spherically shaped dome section and includes a preformed pattern of weakened lines (i.e., scoring 27), it suffers from all of the above-mentioned drawbacks associated with known pressure response members.

FIG. 3A illustrates a perspective view of a pressure response member 10 according to one embodiment of the present disclosure. Pressure response member 10 comprises a concave/convex shaped structure including an exterior flange portion 12 and a flat central portion 14. An angled frustum portion 16 between the flange 12 and central portion 14 provides a truncated cone design shape. While FIG. 3A depicts member 10 having a circular shape, other shapes (such as, for example, rectangular) are contemplated.

When the underside of the flat central portion 14 experiences a predetermined set pressure condition, pressure response member 10 activates in the direction of arrow P. For purposes of this specification, the terms "activate" and "activation" refer to the controlled buckling movement or collapse of frustum portion 16, which causes central portion 14 to move.

Figure 4:
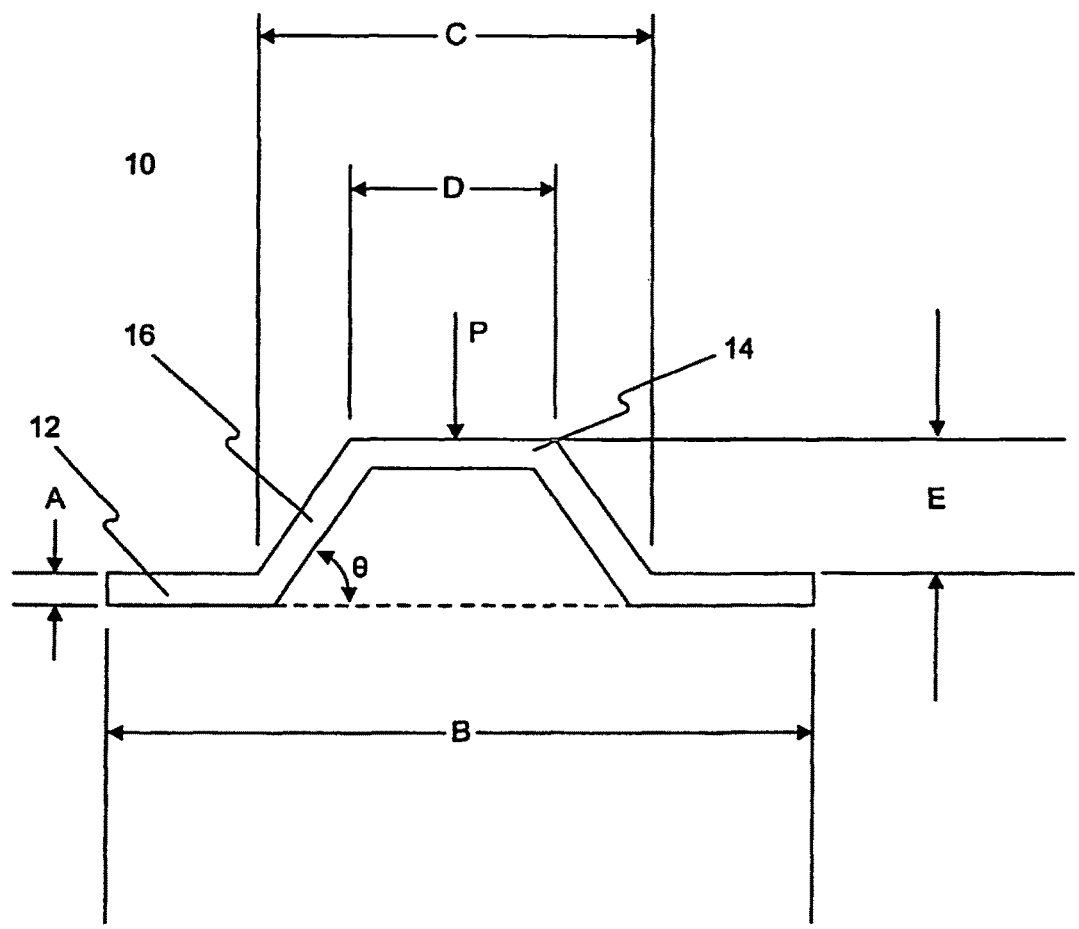
FIG. 4 is a cross-sectional view of the pressure response member of FIG. 3A.

FIG. 4 shows a cross-sectional view of a pressure response member 10. According to FIG. 4, exterior flange portion 12, flat central portion 14, and the angled frustum portion 16 form a truncated cone shape. The embodiment of FIG. 4 depicts frustum angle θ and various design parameters A, B, C, D, and E, which may be selected to provide an activation, or set, pressure P for member 10. For example, frustum angle θ may be selected from the range of about 10 to 60 degrees, with a more likely range of about 15 to 35 degrees to achieve a desired activation pressure P. When member 10 is subjected to activation pressure P, structure 16 will collapse and allow central portion 14 to move in direction of arrow P.

In one embodiment, the truncated cone design could be used in applications where the rupture or bursting of the pressure response member is not desired or required. In such applications, activation movement—and not the bursting of the disk—may trigger an indication signal or other control response. In such an embodiment, pressure response member 10 (as illustrated in FIGS. 3A and 4) may not require the costly further manufacturing process of forming a burst pattern by means of cutting, scoring, or etching lines of weakness (such as formed by score lines 27 in FIGS. 1 and 2).

Figure 3B:
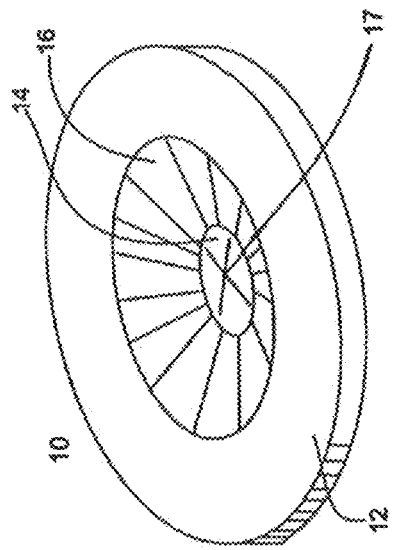
FIG. 3B is a perspective view of a pressure response member having a line of weakness, according to an embodiment of the disclosure.

In other embodiments, a line of weakness may be desired to facilitate burst or rupture. As illustrated in FIG. 3B, central portion 14 may be connected to the frustum portion 16 by a line of weakness 15 (e.g. a score line or an etched groove). In such an embodiment, rupture or opening of central portion 14 is controlled by the shape of the frustum portion 16.

The truncated cone shape of FIGS. 3A and 4 may provide the advantage of a more predictable and consistent activation movement than other generally concave/convex shapes. For example, a truncated cone's "pie-pan" profile generally symmetrically reverses its orientation upon activation. In contrast, a generally spherically shaped domed structure may only partially collapse or may reverse in an irregular, non-symmetrical fashion.

A truncated cone design also may provide the advantage of greater resistance to packaging, shipping, handling, and installation damage. A damaged pressure response member may exhibit diminished performance—it may activate at a lower pressure than the desired, predetermined set pressure. The truncated cone design of FIGS. 3A and 4 resists such damage because it may be thicker (dimension A of FIG. 4) than a comparable spherical member with the same set pressure. Stated another way, for a given material thickness and nominal size, the truncated cone shape gives a reversal pressure of about half compared to a traditional shaped disk. For example, a 0.25" nominal size truncated cone manufactured from aluminum having a thickness of 0.005", has a response pressure approximately 85 psig, whereas a hemispherical shaped structure of the same nominal size, material, and thickness has a response pressure of approximately 160 psig. Accordingly, the truncated cone design achieves a lower response pressure (i.e., greater sensitivity) for the same thickness of material. These material specification differences can result in a thicker disk material that is more resistant to handling damage during shipping and packaging, yet still achieves the same response pressure.

Figure 5A:
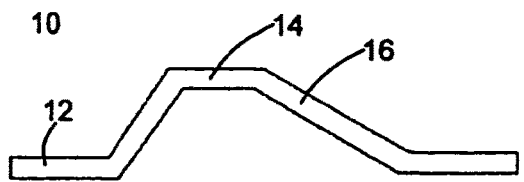
FIG. 5A is a cross-sectional view of a pressure response member having an irregular cone shape.
Figure 5B:
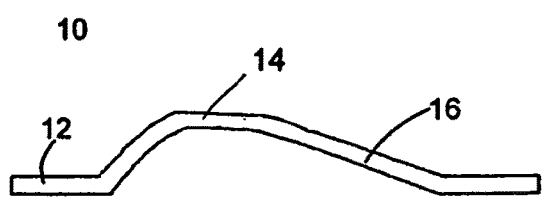
FIG. 5B is a cross-sectional view of a pressure response member having an irregular dome shape.

While the embodiments of FIGS. 3A and 4 illustrate a member 10 comprising a symmetrical truncated cone shape, the present disclosure comprehends irregular cone shapes and irregular dome shapes that also may achieve a reliable response to a predetermined pressure. Examples of these irregular shapes are shown in cross-section in FIGS. 5A (irregular cone) and 5B (irregular dome).

Figure 5C:
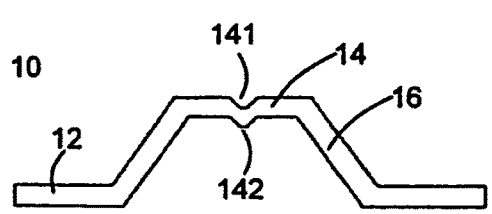
FIGS. 5C-5D depict cross-sectional views of pressure response members having an indentation.
Figure 5D:
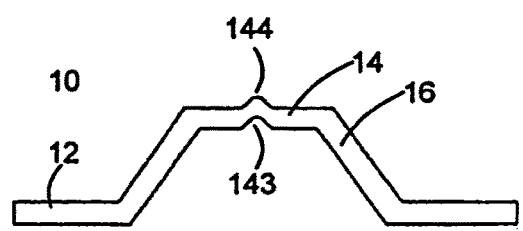

Additional embodiments of a pressure response member 10 may include surface or structural modifications to achieve a desired pressure response. For example, a symmetrical or irregular (non-symmetrical) cone or an irregular spherical dome of member 10 may include at least one indent to its structure. The indent may be formed at or near the apex of the concave/convex shaped structure of member 10. In one embodiment, shown in FIG. 5C, an indentation may be formed in a convex surface of the pressure response member—creating an indented cavity 141 in the convex surface while forming a corresponding nipple-shaped protrusion/dimple 142 in the concave surface. Alternatively, as shown in FIG. 5D, the indentation may be formed in the concave surface of the pressure response member, creating a cavity 143 in the concave surface and a corresponding nipple-shaped protrusion 144 in the convex surface.

Figure 3C:
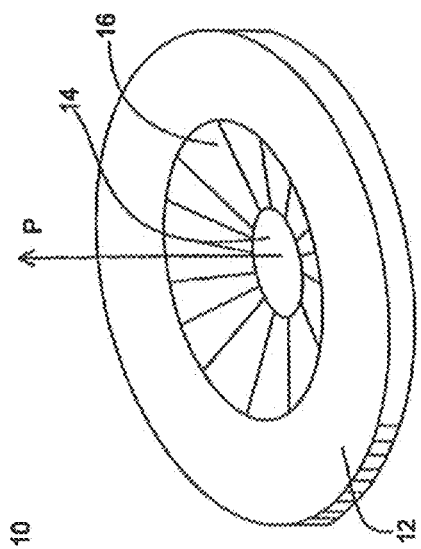
FIG. 3C is a perspective view of a pressure response member having an indentation forming a line, according to an embodiment of the disclosure.
Figure 3D:
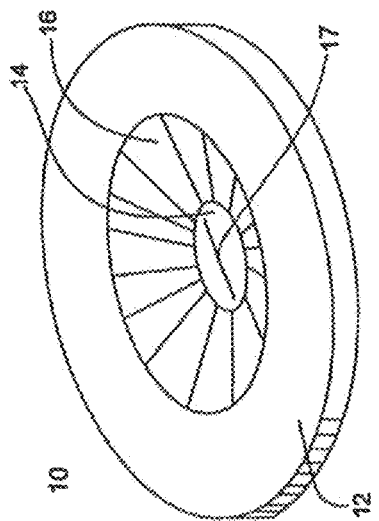
FIG. 3D is a perspective view of a pressure response member having an indentation forming two lines, according to an embodiment of the disclosure.

Another embodiment of pressure response member 10, shown in FIG. 3C, includes an indentation in the form of a straight line 17 having a midpoint coinciding with the apex of the pressure response member 10. In addition, the indentation may include two straight lines 17 that intersect at the apex, as shown in FIG. 3D. It is contemplated that changing the size and shape of the structural apex formation can produce wide variations in the pressure at which a disk of given size and material will buckle. For example, a 1" disk made of 0.003" thick material having a small indentation will buckle at a higher pressure than a similar disk with a larger indentation.

Figure 5E:
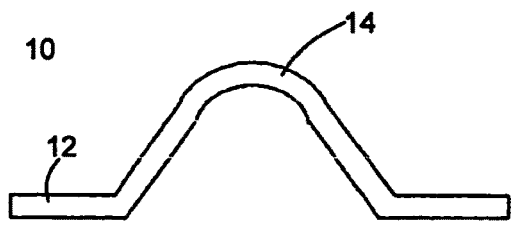
FIGS. 5E-5F depict cross-sectional views of pressure response members having a concave/convex central portion.
Figure 5F:
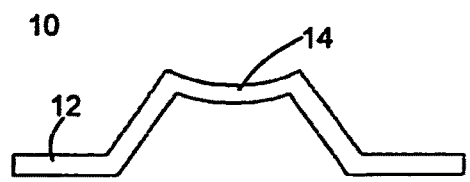

The present disclosure further comprehends providing a central portion 14 that is not flat. Exemplary embodiments shown in FIGS. 5E and 5F provide a central portion 14 that may exhibit a concave/convex shape. Although FIGS. 3A and 4 illustrate a central portion 14 that is substantially flat, and FIGS. 5E and 5F provide central portions 14 that exhibit a concave/convex shape, any other suitable shape of central portion 14 also may be used. Thus, altering the configuration of the central portion 14 and structural apex formation allows a particular size and thickness pressure response member to be adapted to the particular pressure relief needs of a variety of different commercial applications.

For pressure response members of given dimensions A, B, C, D, and E (as shown in FIG. 4) having a flat central portion 14, the response pressure of member 10 is determined by frustum angle θ. Accordingly, in further embodiments, additional structure may be attached to central portion 14 without substantially altering the response pressure of member 10. The additional structure may relate to providing a response control signal upon activation movement of pressure response member 10. Embodiments providing such additional structure are illustrated in FIGS. 6A-12B.

The embodiments shown in FIGS. 6B, 7B, 8B, 9B, 10B, 11B, and 12B depict a relatively flat post-activation shape for member 10; however, the depiction is meant simply to demonstrate a change in displacement distance. In practice, the "pie pan" profile member 10 generally reverses its position upon activation. This general reversal has a tendency to invert and become a generally mirror image of the initial, pre-activation shape. This final shape is not a perfect mirror image of the initial shape and is often irregular and partially distorted, as evidenced by the undulating pattern of member 10 depicted in FIG. 14B. Therefore, it is to be understood that despite the flat shape of member 10 in FIGS. 6B, 7B, 8B, 9B, 10B, 11B, and 12B, the actual post-activation shape will exhibit a generally mirrored, albeit irregular, inverted shape (such as illustrated in FIG. 14B).

Figure 6A:
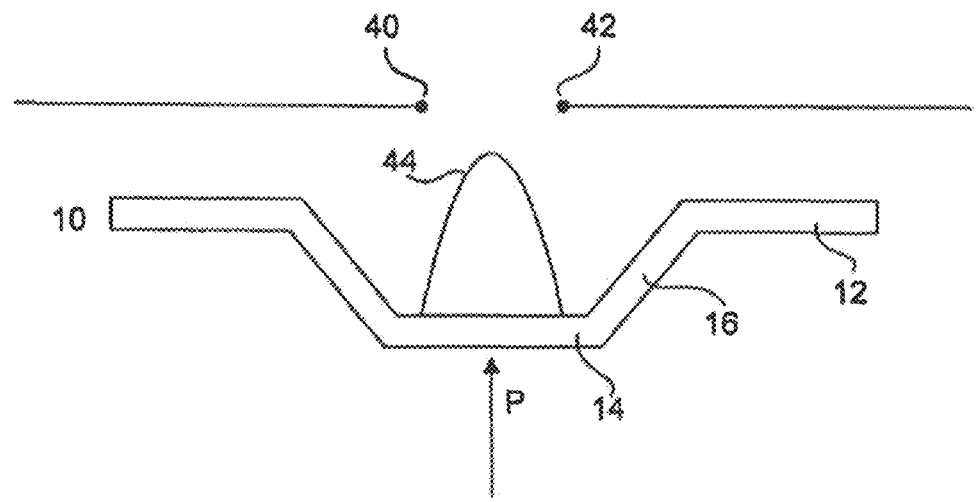
FIGS. 6A-6B depict the use of a pressure response member in a system for closing an electric circuit.
Figure 6B:
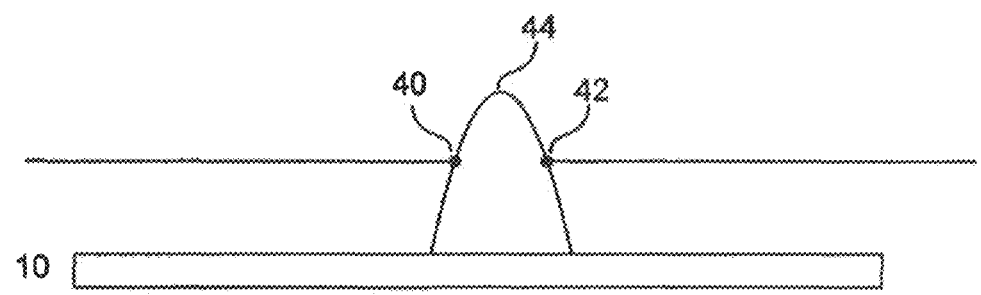

FIGS. 6A-6B depict the use of a pressure response member 10 in a system for closing an electric circuit. As seen in FIG. 6A, an open electrical circuit path is present between circuit terminals 40 and 42. A pressure response member 10 is positioned relative to terminals 40 and 42 of the illustrated electrical circuit path. The central portion 14 of member 10 includes a resilient, electrically conducting spring arch 44. Upon experiencing a predetermined set activation pressure P, the activation movement of member 10 may displace arch 44 into engagement with the terminals 40 and 42, thereby completing an electric circuit as illustrated in FIG. 6B. The completed electric circuit may trigger an alarm or any other suitable response to activation of member 10. In an alternative embodiment (not shown), the arch 44 may include structure (e.g., engagement clips, or mating male and female resilient clip members) for mechanically ensuring continued engagement between arch 44 and the circuit terminal after activation of member 10.

Figure 7A:
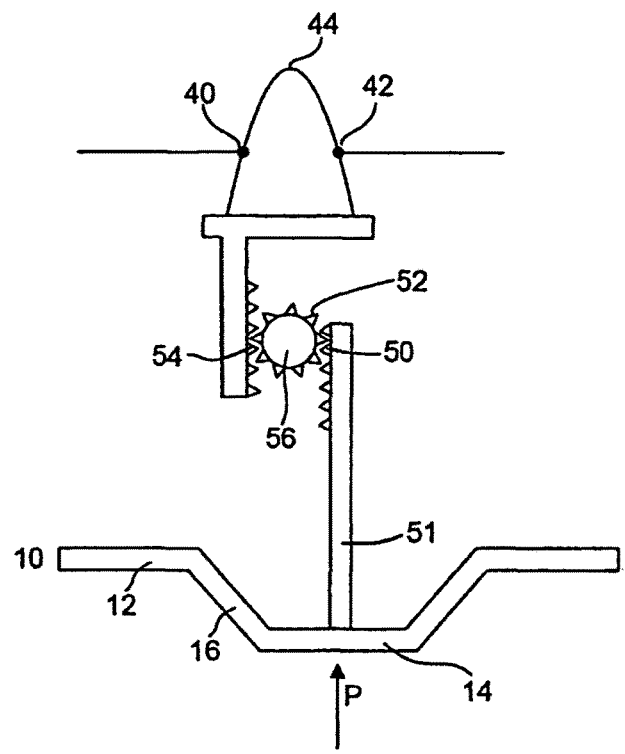
FIGS. 7A-7B depict the use of a pressure response member in a system for opening an electric circuit.
Figure 7B:
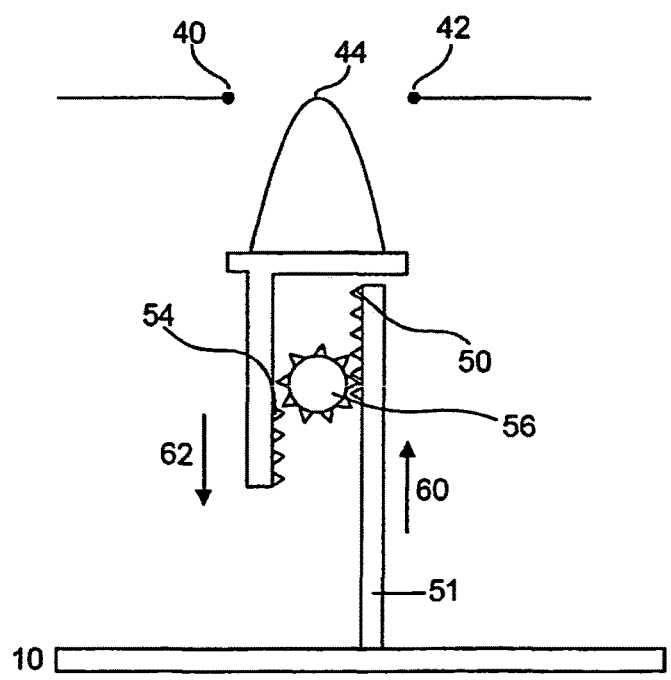

FIGS. 7A-7B depict the use of a pressure response system for opening an electrical circuit upon activation of member 10. In FIG. 7A, the pressure response member 10 is in the inactivated, original position and arch 44 is in position to complete an electrical circuit between terminals 40 and 42. Central portion 14 of member 10 supports a projection 51 including engagement teeth 50, which engage teeth 52 of a rotating gear 56. In turn, teeth 52 of gear 56 engage teeth 54 of a projection 53 that supports arch 44.

As seen in FIG. 7B, upon experiencing a predetermined pressure condition P, the central portion 14 of member 10 may be displaced such that the teeth 50 move in the direction of arrow 60 to engage teeth 52, resulting in counter-clockwise rotation of gear 56, depicted by arrows 58. This rotation, in turn, forces the engagement of teeth 54 with teeth 52, resulting in the movement of arch 44 in the direction of arrow 62, thereby interrupting the electrical circuit between terminals 40 and 44.

Figure 8A:
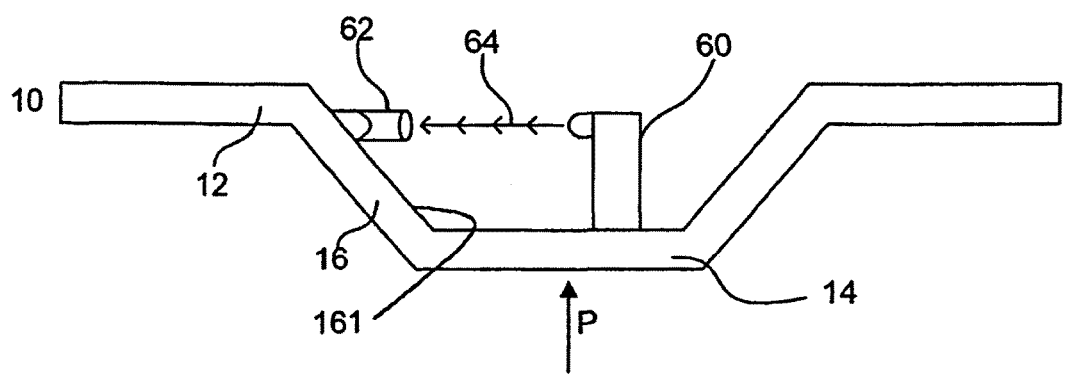
FIGS. 8A-8B depict the use of a pressure response member in another system for opening an electric circuit.

The embodiments of FIGS. 8A-10B depict alternative arrangements utilizing the circuit components of a photo emitter and photo detector to transmit a control signal in response to the activation of pressure response member 10. For example, FIG. 8A depicts a pressure response member 10 incorporating a photo emitter 60 along the central portion 14. The upper surface 161 of the frustum includes a photo detector 62 aligned to detect and acknowledge light signal 64.

Figure 8B:
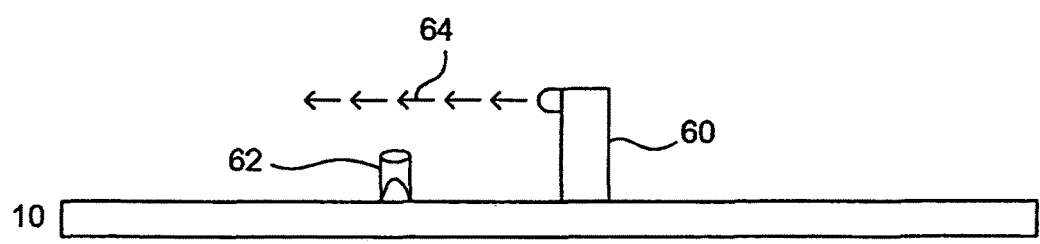

According to the embodiment of FIGS. 8A and 8B, a signal is interrupted upon the activation of member 10. As seen in FIG. 8B, when the pressure P reaches a predetermined set level, pressure response member 10 is activated, resulting in displacement of central portion 14. This displacement of central portion 14 results in a change in orientation between photo emitter 60 and photo detector 62. More particularly, due to the change in orientation between photo emitter 60 and photo detector 62, photo detector 62 no longer recognizes light signal 64. This loss of signal can be used in any electrical circuit to indicate a desired response signal related to the over-pressure condition. Appropriate response signals may include a toggle switch or other conventional voltage divider used in common logic circuitry to designate one of two conditions.

Figure 9A:
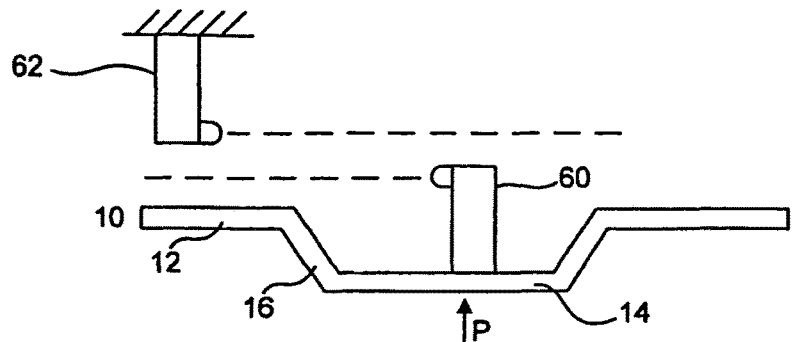
FIGS. 9A-9B depict the use of a pressure response member in a system for aligning a photo emitter and photo detector.
Figure 9B:
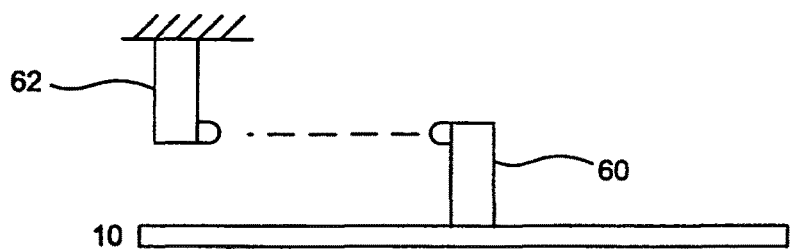
Figure 10A:
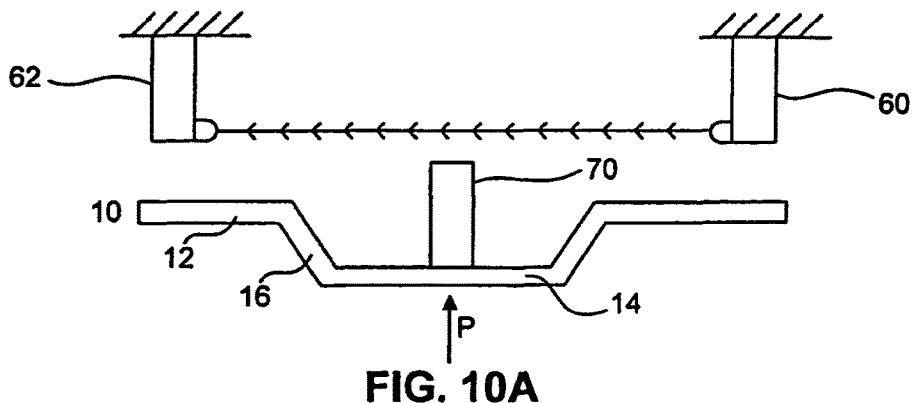
FIGS. 10A-10B depict the use of a pressure response member in a system for disrupting the signal between a photo emitter and photo detector.
Figure 10B:
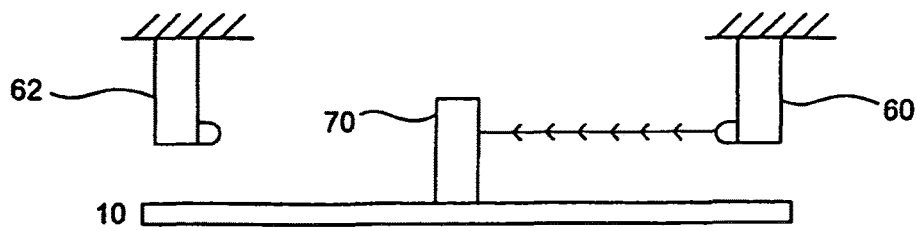

According to the embodiments of FIGS. 9A-10B, a responsive signal is transmitted upon the activation of member 10. For example, FIGS. 9A-9B illustrate an arrangement whereby photo emitter 60 and photo detector 62 are aligned to generate a responsive acknowledgment signal upon activation of member 10. Alternatively, FIGS. 10A-10B illustrate the use of an opaque projection 70 along central portion 14 of member 10, such that upon activation projection 70 disrupts the signal between photo emitter 60 and photo detector 62, thereby resulting in a responsive signal change indicating activation of member 10.

Figure 11A:
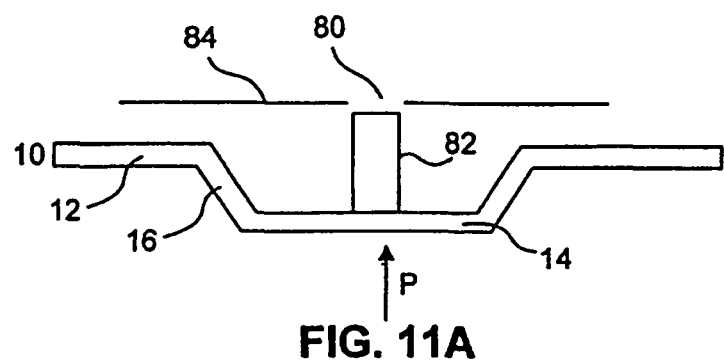
FIGS. 11A-11B depict the use of a pressure response member in a system for visually indicating activation of the pressure response member.
Figure 11B:
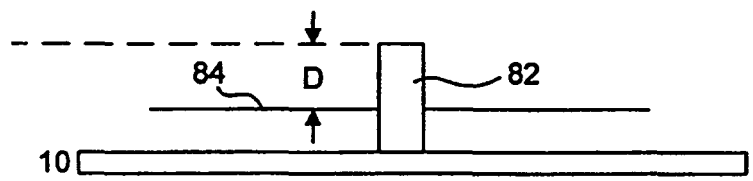

FIGS. 11A-11B depict the use of a pressure response member 10 in a system for visually indicating activation of the pressure response member. The central portion 14 of member 10 in FIG. 11A includes a projection member 82. In its original, pre-activation position, projection 82 is recessed below an aperture 80 along an indication surface 84. Upon activation of pressure response member 10 due to a predetermined pressure force in the direction of arrow P, the projection is displaced through aperture 80 in indication surface 84. Accordingly, upon the occurrence of a predetermined pressure condition, projection 82 is displaced a predetermined distance D above the indication surface 84, thereby visually indicating that member 10 has activated.

Figure 12A:
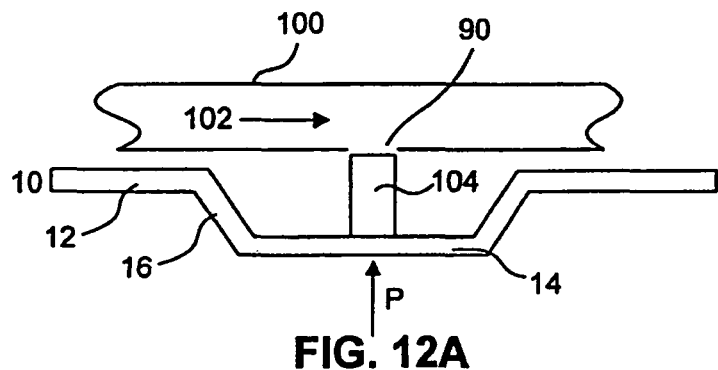
FIGS. 12A-12B depict the use of a pressure response member in a system for closing a fluid path.
Figure 12B:
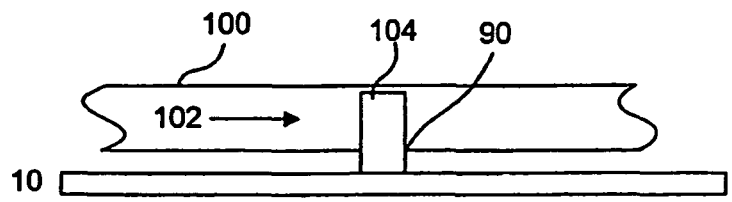

FIGS. 12A-12B illustrate the use of a pressure response member 10 in a system for closing a fluid path. As seen in FIG. 12A, the central portion 14 of member 10 includes a fluid sealing projection 104 aligned with aperture 90 along fluid pipe 100. Fluid pipe 100 is completely separate from the fluid and pressure that causes activation of pressure response member 10. When pressure P activates member 10, the projection 104 projects through aperture 90 into the fluid pipe 100. The final position of sealing projection 104 may block the fluid flow path 102 within pipe 100.

Figure 13A:
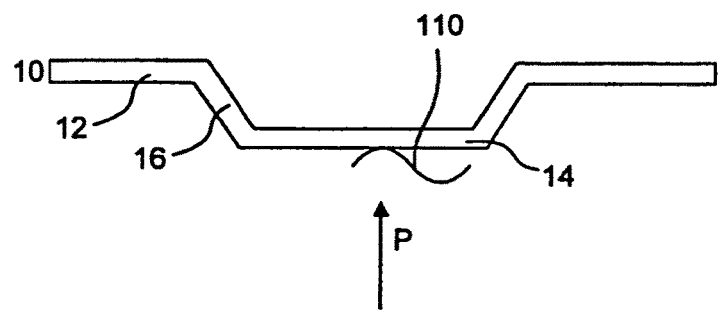
FIGS. 13A-13B depict the use of a pressure response member in a system for effecting electrical interrupt of an electric circuit.
Figure 13B:
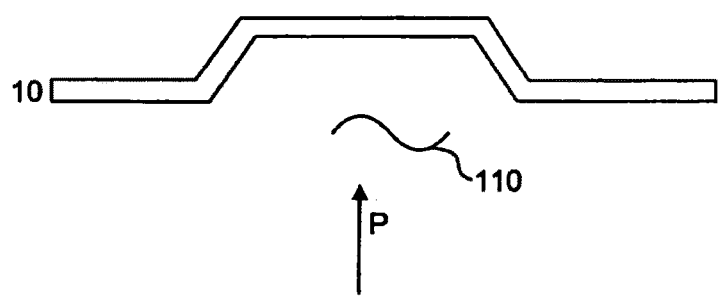

In one embodiment, a pressure response member 10 can be used in a system for interrupting an electrical circuit. FIG. 13A depicts the pre-activation arrangement of member 10. On the inlet side of member 10, conductor 110 makes an electric wire connection with a portion of the central section 14 of pressure response member 10. During use, a pressure force P acts on the inlet side of member 10. As shown in FIG. 13B, when the magnitude of pressure reaches a predetermined set pressure on the inlet side of member 10, pressure response member 10 activates, displacing and generally inverting pressure response member 10. This activation and inversion may interrupt the connection between conductor 110 and member 10. In the post-activation configuration, the pressure response member can be arranged to indicate the activation condition through an electric circuit or electric switch utilizing conductor 110.

Figure 14A:
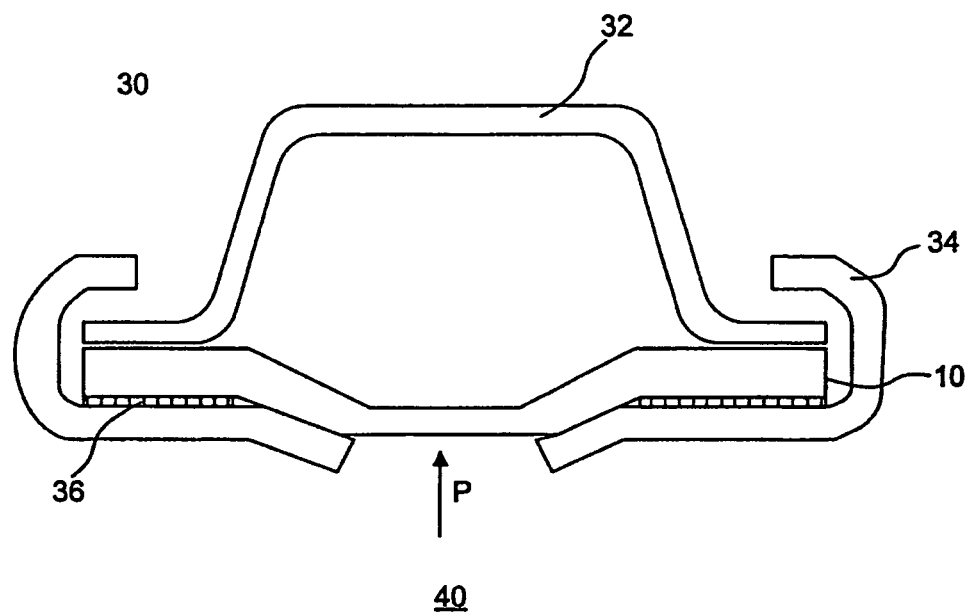
FIG. 14A is a cross-sectional view of a pressure response member used in a system for interrupting a battery circuit, according to an embodiment of the disclosure.
Figure 14B:
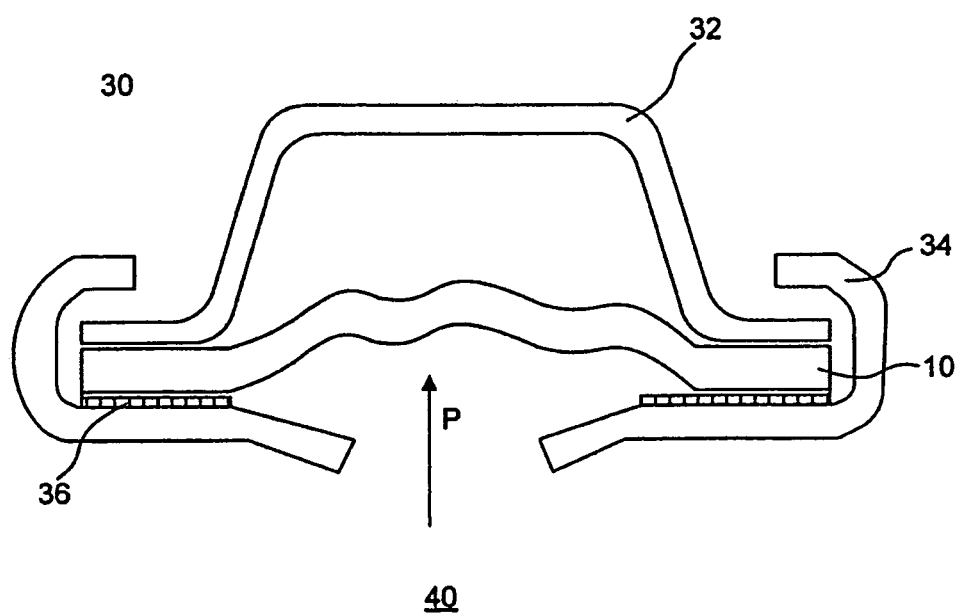
FIG. 14B is a cross-sectional view of the system of FIG. 14A, after activation of the pressure response member, according to an embodiment of the disclosure.

In another embodiment, pressure response member 10 can be used in a system for interrupting a battery circuit, as shown in FIGS. 14A and 14B. FIG. 14A depicts a schematic representation of a battery cell 30. The battery cell 30 includes a terminal contact 32, an electrically conducting jacket 34, a pressure response member 10 exhibiting a truncated cone shape, and an insulating gasket 36 disposed between a portion of the electrically conducting jacket 34 and the pressure response member 10.

The electrical-power-providing components of the battery cell in portion 40 may establish a conducting path at jacket 34. By virtue of contact between jacket 34 and pressure response member 10, an electrical path flows through the system and terminates at terminal contact 32. When a short circuit situation, or any other dangerous, over-pressure situation occurs within the interior portion of battery cell 30, portion 40 experiences increasing pressure. As seen in FIG. 14B, when pressure P reaches a predetermined level, pressure response member 10 activates, thereby breaking the electrically conductive pathway between jacket 34 and pressure response member 10. In the illustrated embodiment, the pressure response member 10 does not include any scoring or line of weakness that causes the member 10 to rupture or burst. Instead, the activation is controlled by virtue of the particular thickness and frustum angle of member 10 (parameters A and θ of FIG. 4).

Typical materials of construction for pressure response member 10 include, but are not limited to, stainless steel, aluminum, nickel or its alloys, carbon, graphite, and plastics. Methods of forming pressure response member 10 include forming or stamping metal coil or sheet material. In addition, manufacturing may include machining of metal, graphite, or plastic material as well as casting, molding, or any combination of the aforementioned manufacturing techniques.

Each of the above described embodiments may be used in combination to provide an alternative response control signal. In addition, components of each of the different embodiments may be substituted and/or combined in any conceivable manner in order to provide a versatile response system.

Figure 15:
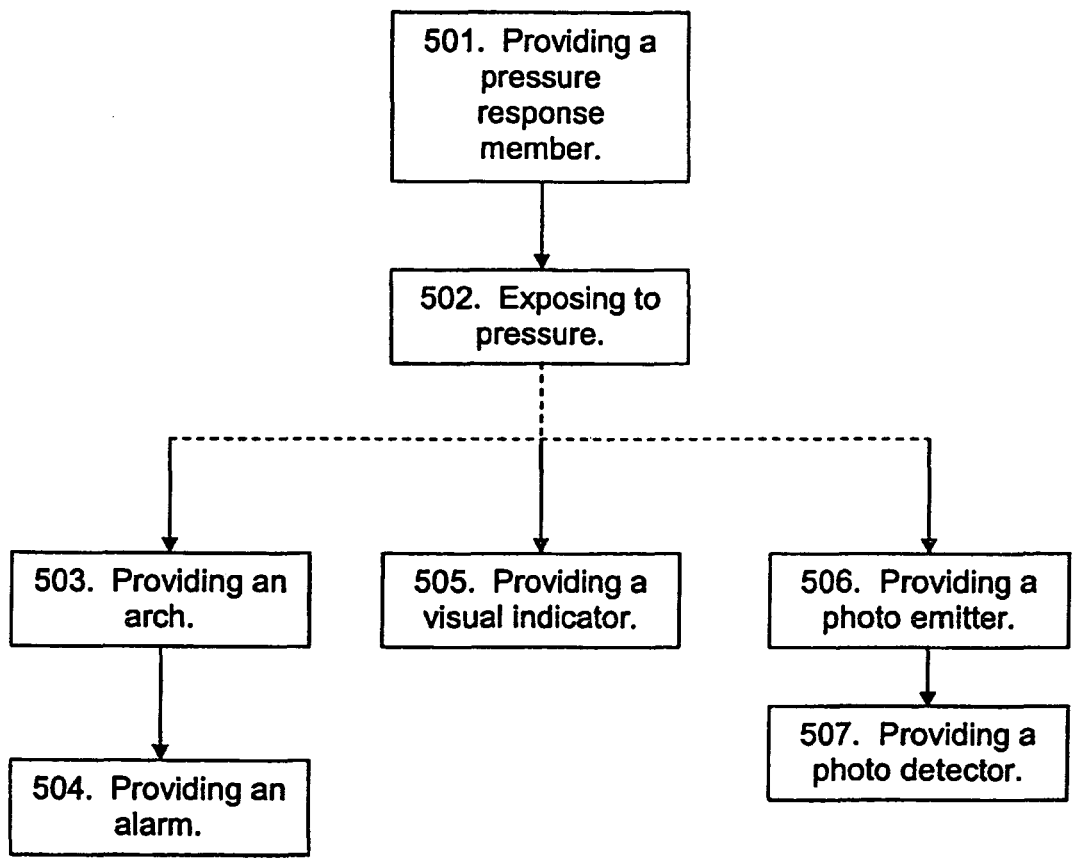
FIG. 15 is a flow chart depicting a method for testing a pressure response member, according to an embodiment of the disclosure.

Turning to use of the above described embodiments, FIG. 15 depicts a flow-chart for a method of responding to an overpressure situation. One embodiment includes providing a pressure response member 501, which includes a flange portion, a central portion, and an angled frustum portion positioned between the flange portion and the central portion. The angled frustum portion is configured to activate by buckling and reversing under a predetermined level of pressure—moving from a first configuration to a second configuration. The pressure response member is exposed to a pressure source 502, such that the pressure response member responds to a predetermined pressure in the pressure source by taking the second configuration.

In another embodiment, a method for responding to an overpressure situation also may include attaching a conductive arch 503 to the central portion. The pressure response member may be positioned relative to an open circuit including a first terminal end and a second terminal end, such that the conductive arch completes the open circuit between the first terminal end and the second terminal end when the pressure response member takes the second configuration. A method also may include providing an alarm 504 configured to indicate activation, wherein completing the open circuit between the first terminal end and the second terminal end triggers the alarm. While a method providing an alarm is described, a method providing any other suitable indication or action in response to activation is also comprehended.

Another embodiment includes providing structure configured to provide visual indication of a response 505. Such structure may include, for example, a projection attached to the central portion, configured to project through an aperture of a visual indication surface after activation.

As shown in FIG. 15, a method also may include providing a photo emitter 506 configured to communicate with a photo detector 507. In one embodiment, the photo detector may be aligned to communicate with the photo emitter before activation, when the pressure response member is in a first configuration. In another embodiment, the photo detector may be aligned to communicate with the photo emitter after activation, when the pressure response member is in a second configuration.

It is a further object of this disclosure to describe alternative methods for testing the pressure response members described herein. As noted above, a pressure response member may activate without rupture or bursting of the pressure response member 10. Accordingly, since there is no abrupt venting of extreme pressure, there is no abrupt change in system pressure that can be documented to test such a pressure response member to determine accuracy and maintain quality control. In addition, the noise produced by the activation of pressure response member 10 is often insufficient to be detected in a busy workshop environment. Therefore alternative methods and testing mechanisms are useful in testing such a pressure response member to determine accuracy and maintain quality control.

Figure 16:
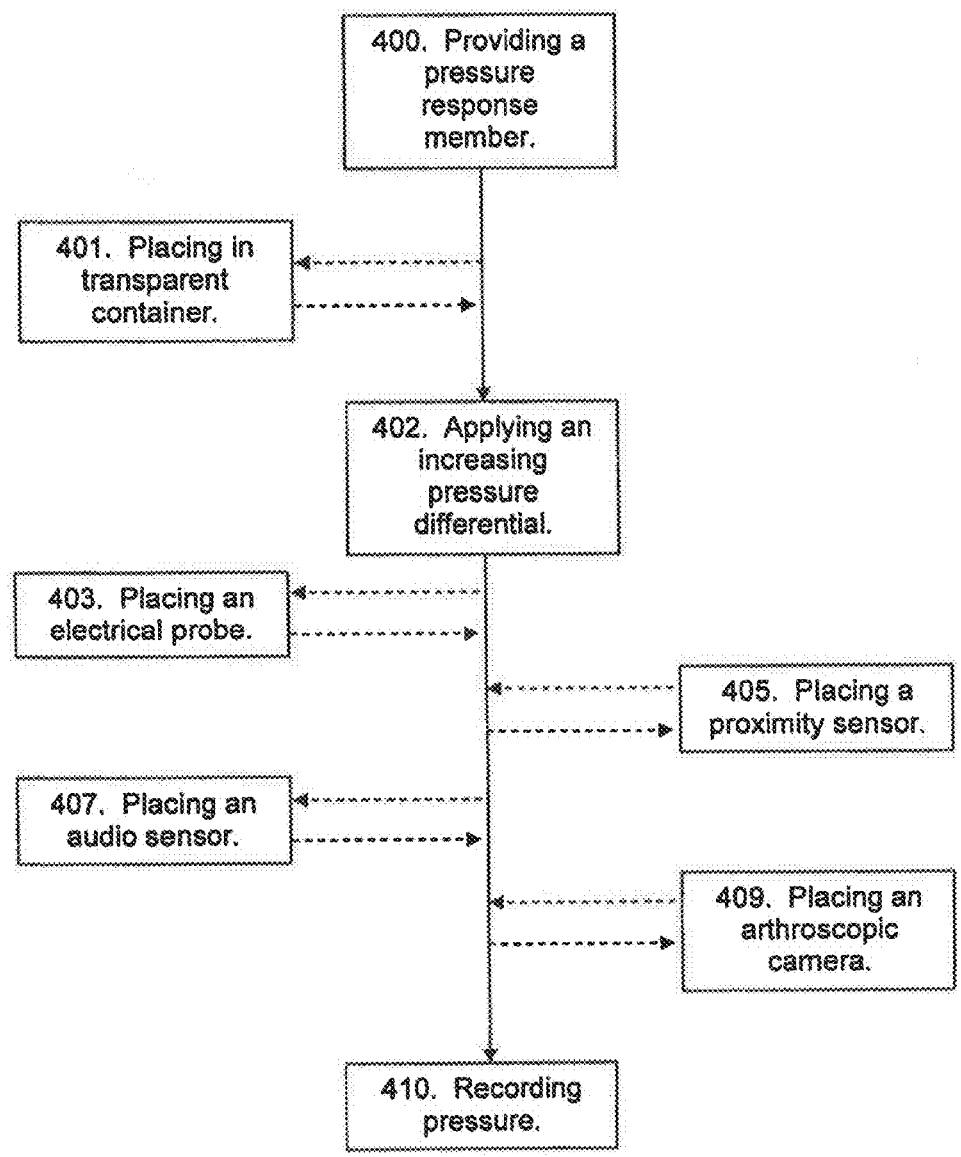
FIG. 16 is a flow chart depicting a method for responding to pressure, according to an embodiment of the disclosure.

According to one embodiment, illustrated in FIG. 16, a method for testing a pressure response member includes providing a pressure response member 400, the pressure response member including a flange portion, a central portion, and an angled frustum portion provided between the flange portion and the central portion. An increasing pressure differential may be applied to the pressure response member 402, and a user may record the pressure 410 at which the pressure response member activates.

Another method for testing a pressure response member may further include placing a pressure response system within a transparent container 401 to allow visual indication of the moment when member activates.

Further methods for testing a pressure response member may optionally include placing an electrical probe 403 in a position to contact the member only upon activation of the member, or placing a proximity sensor 405 on the outlet side of member 10 in order to measure and record the precise moment of activation. Exemplary proximity sensors may include, but are not limited to, a dual magnet arrangement, hall effect sensors, or known telemetry devices.

Another embodiment may include placing an audio sensor 407 (e.g., a miniature microphone) with appropriate amplification in relation to the testing chamber and mounting structure in order to precisely detect movement of the pressure response member 10. In another embodiment, an arthroscopic camera 409 may be appropriately aligned within the testing chamber and mounting structure in order to record movement of the convex/concave structure.

Other embodiments will be apparent to those skilled in the art from consideration of the specification and practice of the disclosure herein. It is intended that the specification and examples be considered as exemplary only, with a true scope and spirit of the disclosure being indicated by the following claims.

What is claimed is:

1. A pressure response device comprising:
   a flange portion;
   a central portion, the central portion having an inlet side and an outlet side;
   an angled frustum portion provided between the flange portion and the central portion, wherein the angled frustum portion is configured to activate upon experiencing a predetermined pressure differential causing the movement of the central portion; and
   a conductor, the conductor configured to make an electrical wire connection with the central portion before the angled frustum portion activates; and
   wherein the electrical wire connection is interrupted when the angled frustum portion activates;
   wherein the angled frustum portion defines an angle with the flange portion; and
   wherein the frustum angle is configured to set a predetermined pressure differential at which the pressure response device will activate and displace the central portion.

2. The device of claim 1, wherein an angle between the angled frustum portion and a plane defined by the flange portion is between about 10 degrees and about 60 degrees.

3. The device of claim 1, wherein an angle between the angled frustum portion and a plane defined by the flange portion is between about 15 degrees and about 35 degrees.

4. The device of claim 1, wherein the angled frustum portion is in the shape of a symmetrical truncated cone, an irregular truncated cone, or an irregular truncated dome.

5. The device of claim 1, wherein the central portion further comprises an indentation.

6. The device of claim 5, wherein the indentation defines a cavity in the inlet side of the central portion and wherein the indentation defines a nipple in the outlet side of the central portion.

7. The device of claim 5, wherein the indentation defines a cavity in the outlet side of the central portion and wherein the indentation defines a nipple in the inlet side of the central portion.

8. The device of claim 5, wherein the indentation defines a line, the line having a midpoint coinciding with an apex of the pressure response device.

9. The device of claim 5, wherein the indentation defines a first line and a second line, the first line and second line intersecting at an apex of the pressure response device.

10. The device of claim 1, further comprising a line of weakness formed between the central portion and the angled frustum configured to facilitate activation of the device.

* * * * *